United States Patent
York-Leung Wong

(10) Patent No.: US 7,878,187 B2
(45) Date of Patent: Feb. 1, 2011

(54) HEAT CELLS COMPRISING EXOTHERMIC COMPOSITIONS HAVING ABSORBENT GELLING MATERIAL

(75) Inventor: Vincent York-Leung Wong, Hamilton, OH (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/233,916

(22) Filed: Sep. 23, 2005

(65) Prior Publication Data

US 2007/0068508 A1    Mar. 29, 2007

(51) Int. Cl.
  *F24J 1/00* (2006.01)
  *F24J 3/00* (2006.01)

(52) U.S. Cl. .................. 126/263.01; 126/263.02; 602/62; 607/108

(58) Field of Classification Search .......... 607/114, 607/108; 126/263.01, 263.05, 263.06, 263.02; 252/67, 373; 44/252, 253; 75/707, 505, 75/387, 495, 490, 384, 379, 496, 497, 641, 75/444, 450, 493, 464; 266/141, 187, 197, 266/83, 139, 156, 140, 147, 186, 148, 171; 423/138, 322; 48/213; 432/222; 422/139; 60/772; 602/62

See application file for complete search history.

(56) References Cited

U.S. PATENT DOCUMENTS

| | | | |
|---|---|---|---|
| 2,243,110 A | 5/1941 | Madaras | |
| 2,793,946 A | 5/1957 | Paschal | |
| 2,807,535 A | 9/1957 | Segre | |
| 2,900,247 A | 8/1959 | Celada | |
| 2,915,379 A | 12/1959 | Agarwal | |
| 3,128,174 A | 4/1964 | Celada | |
| 3,136,623 A | 6/1964 | Mader et al. | |
| 3,136,624 A | 6/1964 | Mader et al. | |
| 3,136,625 A | 6/1964 | Mader et al. | |
| 3,301,250 A | 1/1967 | Glasser | |
| 3,375,098 A | 3/1968 | Marshall | |
| 3,423,201 A | 1/1969 | Celada et al. | |
| 3,643,665 A | 2/1972 | Caillouette | |
| 3,684,486 A | 8/1972 | Osman | |
| 3,765,872 A | 10/1973 | Celada et al. | |
| 3,770,421 A | 11/1973 | Celada et al. | |
| 3,779,741 A | 12/1973 | Celada et al. | |
| 3,816,102 A | 6/1974 | Celada et al. | |
| 3,827,879 A | 8/1974 | Celada et al. | |
| 3,865,117 A | 2/1975 | Perry | |
| 3,874,504 A | 4/1975 | Verakas | |
| 3,890,142 A | 6/1975 | Celada et al. | |
| 3,904,397 A | 9/1975 | Celada et al. | |
| 3,940,905 A | 3/1976 | Perry | |
| 4,055,188 A | 10/1977 | Pelton | |
| 4,095,583 A | 6/1978 | Petersen et al. | |
| 4,106,478 A | 8/1978 | Higashijima | |
| 4,366,804 A | 1/1983 | Abe | |
| 4,649,895 A | 3/1987 | Yasuki et al. | |
| 4,856,651 A | 8/1989 | Francis | |
| 4,953,550 A | 9/1990 | Dunshee | |
| 5,046,479 A | 9/1991 | Usui | |
| 5,233,981 A | 8/1993 | Miyashita | |
| 5,342,412 A | 8/1994 | Ueki | |
| 5,366,492 A | 11/1994 | Ueki | |
| 5,471,767 A | 12/1995 | Walker | |
| 5,534,021 A | 7/1996 | Dvoretzky et al. | |
| 5,545,197 A | 8/1996 | Bowen | |
| 5,658,583 A | 8/1997 | Zhang et al. | |
| 5,662,624 A | 9/1997 | Sundstrom et al. | |
| 5,674,270 A | 10/1997 | Viltro et al. | |
| 5,728,146 A | 3/1998 | Burkett et al. | |
| 5,837,005 A | 11/1998 | Viltro et al. | |
| 5,860,945 A * | 1/1999 | Cramer et al. | 602/62 |
| 5,879,378 A | 3/1999 | Usui | |
| 5,918,590 A * | 7/1999 | Burkett et al. | 126/263.02 |
| 5,925,072 A | 7/1999 | Cramer et al. | |
| 5,980,562 A | 11/1999 | Ouellette et al. | |
| 5,984,995 A * | 11/1999 | White | 75/230 |
| 6,019,782 A | 2/2000 | Davis et al. | |
| 6,020,040 A | 2/2000 | Cramer et al. | |
| 6,024,761 A | 2/2000 | Barone et al. | |
| 6,048,326 A * | 4/2000 | Davis et al. | 602/26 |
| 6,074,413 A | 6/2000 | Davis et al. | |
| 6,096,067 A | 8/2000 | Cramer et al. | |

(Continued)

FOREIGN PATENT DOCUMENTS

EP    1332740    8/2003

(Continued)

OTHER PUBLICATIONS

U.S. Appl. No. 11/233,738, filed Sep. 23, 2005, Wong, Vincent York-Leung et al.

(Continued)

*Primary Examiner*—Kenneth B Rinehart
*Assistant Examiner*—Chuka C Ndubizu
(74) *Attorney, Agent, or Firm*—Joel Silver; Jeffrey M. Gold

(57) ABSTRACT

The present invention is directed to heat cells that are suitable for incorporation into disposable heating wraps. The heat cells comprise an exothermic composition comprising an absorbent gelling material, wherein the absorbent gelling material provides for improved heat application in the relief of temporary or chronic body aches and pains.

19 Claims, No Drawings

U.S. PATENT DOCUMENTS

| | | |
|---|---|---|
| 6,099,556 A | 8/2000 | Usui |
| 6,102,937 A | 8/2000 | Cramer et al. |
| 6,123,717 A | 9/2000 | Davis et al. |
| 6,158,427 A | 12/2000 | McQuire et al. |
| 6,336,935 B1 | 1/2002 | Davis et al. |
| 6,409,746 B1 | 6/2002 | Igaki et al. |
| 6,436,126 B1 | 8/2002 | McAfee |
| 6,453,648 B1 | 9/2002 | Zhang et al. |
| 6,484,514 B1 * | 11/2002 | Joseph et al. ............... 62/4 |
| 6,629,964 B1 | 10/2003 | Ono et al. |
| 6,652,771 B2 | 11/2003 | Carn |
| 6,791,004 B2 | 9/2004 | Sprengard-Eichel et al. |
| 6,863,682 B2 | 3/2005 | Usui |
| 6,881,219 B1 | 4/2005 | Agarwal et al. |
| 6,893,453 B2 | 5/2005 | Agarwal et al. |
| 7,041,123 B2 | 5/2006 | Stapf et al. |
| 7,060,086 B2 | 6/2006 | Wilson et al. |
| 7,087,076 B2 | 8/2006 | Purcell |
| 2002/0020406 A1 * | 2/2002 | Minami ............... 126/263.02 |
| 2003/0097164 A1 | 5/2003 | Stapf et al. |
| 2004/0015220 A1 | 1/2004 | Um et al. |
| 2004/0042965 A1 * | 3/2004 | Usui et al. ............... 424/40 |
| 2004/0116023 A1 | 6/2004 | Huang et al. |
| 2004/0116990 A1 | 6/2004 | Agarwal et al. |
| 2004/0178384 A1 * | 9/2004 | Usui ............... 252/76 |
| 2004/0217325 A1 | 11/2004 | Usui et al. |
| 2004/0261783 A1 | 12/2004 | Madan et al. |
| 2006/0276863 A1 | 12/2006 | Kumamoto et al. |
| 2006/0282138 A1 | 12/2006 | Ota |
| 2007/0021810 A1 | 1/2007 | Paulin |
| 2007/0055329 A1 | 3/2007 | Hicks et al. |
| 2008/0200971 A1 * | 8/2008 | Dodo ............... 607/108 |
| 2008/0283038 A1 | 11/2008 | Dodo |

FOREIGN PATENT DOCUMENTS

| | | |
|---|---|---|
| EP | 1577363 A1 * | 9/2005 |
| EP | 1655005 | 5/2006 |
| GB | 2205496 | 12/1998 |
| GB | 2 393 732 A | 4/2004 |
| JP | 57207748 | 12/1982 |
| JP | 56165223 | 4/1983 |
| JP | 5989029 | 12/1984 |
| JP | 60106874 | 6/1985 |
| JP | H31856 | 1/1991 |
| JP | 6343658 | 12/1994 |
| JP | 8206147 | 12/1996 |
| WO | 03010344 | 2/2003 |
| WO | WO 2005/118740 A | 12/2005 |

OTHER PUBLICATIONS

International Search Report PCT/IB2006/053443-Mailed Oct. 24, 2008.

Allen, Terrence, "Methods of Presenting Size Analysis Data", Particle Size Measurement, 1990, $4^{th}$ Edition, pp. 153-156.

Bakker, Marilyn, "Thermoforming", The Wiley Encyclopedia of Packaging Technology, 1986, pp. 668-675.

Riedel, "Nonwoven Bonding Methods and Materials", Nonwoven World, 1987.

* cited by examiner

HEAT CELLS COMPRISING EXOTHERMIC COMPOSITIONS HAVING ABSORBENT GELLING MATERIAL

FIELD OF THE INVENTION

The present invention is directed to heat cells that are suitable for incorporation into disposable heating wraps. In particular, the present invention is directed to heat cells that comprise an exothermic composition comprising an absorbent gelling material, wherein the absorbent gelling material provides for improved heat application.

BACKGROUND OF THE INVENTION

Disposable heat wraps have become a popular application of applying heat to relieve discomfort of temporary or chronic body aches and pains. These disposable heat wraps typically comprise an exothermic composition for generating heat, wherein the exothermic composition typically comprises metal powder, salts, and water that allows the exothermic composition to release heat upon oxidation of the metal powder. The heat treatments provided by the disposable heat wraps have been found suitable for treatment of aches and pains associated with stiff muscles and joints, nerve pain, back pain, rheumatism, and the like.

Disposable heating devices can provide sustained heat for periods of from about one hour to about twenty-four hours, and are described as being less messy and more convenient to use that other conventional heat sources such as whirlpools, hot towels, hydrocollators, heating pads and elastic compression bands. Disposable heating devices are further described as satisfactory devices that can maintain consistent and controlled temperature, see for example U.S. Pat. No. 5,918,590 where it is disclosed that heat cells based on specific iron oxidation chemistry are suitable for incorporation into disposable body wraps to provide sustained temperature resulting in consistent, convenient, and comfortable heat application for treating temporary or chronic pain.

It has been found, however, that while sustaining temperature for periods of up to about twenty-four hours, the consistency of the sustained temperature can be improved. One approach of enhancing exothermic reactions is the incorporation of carbon materials such as activated and non-activated carbon materials. Other approaches include the addition of water-retainers or water-holding materials. See for example, the disposable heating devices disclosed in U.S. Pat. Nos. 6,436,126; 6,099,556; and 5,233,981. See also the heating devices disclosed in U.S. Published Patent Application Nos. 2004/0042965 and 2004/0178384.

One specific example of an exothermic composition comprising a water-absorptive polymer is disclosed in U.S. Patent Application Publication No. 2002/0020406. This publication discloses a united exothermic medium wherein an exothermic agent is mixed with a water-absorptive polymer and then the agent/polymer mixture is pressed together with alcohol, a crosslinking agent, or a plasticizer at a certain pressure, to be thereby united.

Despite the disclosures in the art of disposable heating devices comprising exothermic compositions, the need still exists for a specific heating device that comprises an exothermic composition that provides for controlled and sustained temperature throughout the heating period. It is known that the thermal performance of heat cells is highly sensitive to moisture level, and a typical heat cell can comprise water concentrations at or above about 27% to sustain the heating temperature of the heat cell. However, the inclusion of high concentrations of water at levels of about 27% or above can result in slower than desired initial heating temperatures. Therefore, the ability to rapidly reach the desired temperature for a therapeutic benefit and the ability to sustain the temperature are difficult to achieve.

Moreover, current heating devices contain exothermic compositions that are highly prone to segregation effects. It is believed that the particle size differences between the compositional components can contribute to particle segregation. For example, heating devices containing an exothermic composition that comprises water-retainers (e.g., vermiculite, wood flour, absorbing gelling material) in combination with iron powder and carbon have a tendency to segregate. Typically, the particle size of the water retainer is quite large when compared to the iron and carbon particles. For example, current heating devices can comprise exothermic compositions wherein the mean particle size of the water retainer to iron particles is often 10:1 or more, resulting in high particle segregation.

Changes in particle mix composition due to segregation could lead to product thermal performance that is less than optimal and/or different from the intended design. Thus, maximum reaction efficiency is typically not achieved with current heating devices since excess exothermic composition is needed to compensate for particle segregation effects. These heating devices typically comprise heat cells that have relatively large volumes which allow them to accommodate for the excess exothermic composition.

It has been found that heat cells comprising an exothermic composition that comprises an absorbent gelling material are especially effective in rapidly reaching initial heating temperatures as well as being effective in maintaining a consistent temperature for periods up to twenty-four hours. When used in select ratios with other compositional ingredients, it has been found that the absorbent gelling material provides for improved heat application in addition to providing for exothermic compositions that resist compositional changes such as segregation. To provide minimal or no segregation effects, the exothermic compositions of the present invention comprise select particle size ratios of absorbent gelling material to iron powder.

The heat cells of the present invention have adaptable physical dimensions which provide for the heat cells to be incorporated into disposable heating devices such as back wraps, knee wraps, body wraps, joint wraps, menstrual wraps, neck-to-arm wraps, and so forth.

SUMMARY OF THE INVENTION

The present invention is directed to a heat cell comprising a particulate exothermic composition wherein the particulate exothermic composition comprises (a) from about 10% to about 90% by weight of iron powder; (b) from about 1% to about 25% by weight of a carbon selected from the group consisting of activated carbon, non-activated carbon, and mixtures thereof; (c) from about 1% to about 25% by weight of an absorbent gelling material having a median particle size of from about 300 μm to about 800 μm; and (d) from about 1% to about 35% by weight of water; wherein the particles of the particulate exothermic composition are combined in a pocket, formed in a unified structure comprising at least two opposed surfaces, wherein at least one surface is oxygen permeable.

It has been found that the temperature consistency of disposable heating devices can be improved, whereby the heating devices provide sustained heat for periods up to twenty-four hours. Such heating devices comprise specifically defined heat cells, wherein the heat cells comprise an exothermic composition having an absorbent gelling material. The absorbent gelling material enables the retention of water within the particulate exothermic compositions such that the water is released at a controlled rate to result in oxidation of the iron powder, which results in the particulate exothermic compositions providing long lasting heat generation with improved sustained temperature.

It has also been found that particulate exothermic compositions can undergo segregation effects during processing of the exothermic composition, resulting in exothermic compositions that may not provide for maintained consistent and controlled temperatures. To provide minimal or no segregation effects, the particulate exothermic compositions of the present invention comprise select median particle size ratios of absorbent gelling material to iron powder of from about 10:1 to about 1:10, preferably from about 7:1 to about 1:7, more preferably from about 5:1 to about 1:5, and most preferably from about 3:1 to about 1:3.

DETAILED DESCRIPTION OF THE INVENTION

The heat cells of the present invention comprise particulate exothermic compositions. The particulate exothermic composition provides for improved sustained temperature when the heat cells are incorporated into disposable heating devices to relieve discomfort of temporary or chronic body aches and pains.

The exothermic compositions of the present invention are particulate exothermic compositions. As used herein "particulate" refers to separate particles contained within the compositions. In other words, the particulate exothermic compositions defined herein contain separate particles wherein each particle has a median particle size ranging from about 25 µm (microns) to about 800 µm.

Variations in the particle size of the particulate components of the exothermic compositions defined herein can lead to particle separation or segregation within an exothermic composition. In other words, particle size directly effects particle mobility, and the particulate components defined herein can vary in their mobility resulting in particle separation or segregation. The exothermic compositions defined herein preferably comprise particulate components having defined median particle size ranges such that the exothermic compositions resist particle separation or segregation. It is contemplated, however, that particulate components having median particle sizes ranges above or below the ranges defined herein are suitable for use in the exothermic compositions defined herein.

As used herein "sustained temperature" refers to temperatures ranging from about 32° C. to about 50° C., preferably from about 32° C. to about 45° C., more preferably from about 32° C. to about 40° C., and most preferably from about 32° C. to about 37° C. for a period of from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment such that the desired therapeutic benefits are achieved without any adverse events such as skin burns which may be incurred by using a high temperature for a long period of time. Maintaining a "sustained temperature" provided by the particulate exothermic compositions of the present invention has been shown to substantially relieve acute, recurrent, and/or chronic pain including skeletal, muscular, and/or referred pain, of a person having such pain, and to substantially prolong relief even after a disposable heating device comprising the particulate exothermic composition is removed from the afflicted body part without any adverse events.

As used herein, the term "disposable" refers to devices that are intended to be thrown away after extended use. In other words, "disposable" heating devices defined herein are those devices that are meant to be deposited in a suitable trash receptacle after the heating device has been fully extended in the release of heat provided by the heat cells of the present invention. The disposable heating devices defined herein can be stored in a resealable, substantially air-impermeable container for repeated use in the relief of temporary or chronic body aches and pain until the disposable heating device has been fully extended in the release of heat.

The heat cells of the present invention comprise a particulate exothermic composition, wherein the particulate exothermic composition can comprise, consist of, or consist essentially of the elements and limitations of the invention described herein, as well as any of the additional or optional ingredients, components, or limitations described herein.

All percentages, parts and ratios are by weight of the particulate exothermic compositions, unless otherwise specified. All such weights as they pertain to listed ingredients are based on the specific ingredient level and, therefore, do not include carriers or by-products that may be included in commercially available materials, unless otherwise specified.

All documents cited herein, including publications, patent applications, and issued patents mentioned herein, are, in relevant part, incorporated herein by reference. Citation of any document is not an admission regarding any determination as to its availability as prior art to the present invention.

Heat Cell

The present invention is directed to heat cells that comprise a particulate exothermic composition. The heat cells can be incorporated into disposable heating devices to provide for improved sustained temperature in the relief of temporary or chronic body aches and pain. The heat cells are preferably incorporated into the disposable heating devices as a plurality of heat cells.

The heat cell is formed in a unified structure comprising at least two opposed surfaces, preferably, film layer substrate surfaces, wherein at least one surface is oxygen permeable, that when filled with a particulate exothermic composition, has a fill volume, void volume, and a cell volume. The fill volume, as used herein, means the volume of the particulate composition in the filled heat cell. The void volume, as used herein, means the volume of the cell left unfilled by the particulate composition in a finished heat cell, measured without differential pressure in the heat cell and without additional stretching or deformation of the substrate material. The cell volume, as used herein, means the fill volume plus the void volume of the heat cell. The ratio of fill volume to cell volume is from about 0.7 to about 1.0, preferably from about 0.75 to about 1.0, more preferably from about 0.8 to about 1.0, even more preferably from about 0.85 to about 1.0, and most preferably from about 0.9 to about 1.0.

The heat cell can also be measured in terms of its apex. The apex of heat cells defined herein have a height of from greater than about 0.2 cm (centimeters) to about 1.0 cm, preferably from greater than about 0.3 cm to about 0.9 cm, more preferably from about 0.4 cm to about 0.8 cm, and most preferably from about 0.5 cm to about 0.7 cm.

As previously stated, the heat cell is formed in a unified structure comprising at least two opposed surfaces, preferably film layer substrate surfaces. The film layer substrates are preferably made of films or films laminated to nonwoven fabrics. In general the preferred films are those having heat sealability and are capable of being easily thermally fused. Nonwoven, if used, provide support and integrity to the film layer substrates. Examples of suitable films include polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, and synthetic rubber. The film layer substrates thickness is in the range of about 1 to about 300 μm and may be oxygen permeable or impermeable. For the non-woven fabrics, those having preferred characteristic properties of light weight and high tensile strength, e.g., nylon, rayon, cellulose ester, polyvinyl derivatives, polyolefins, polyamides, or polyesters, cuproammonium cellulose (Bemberg) and other high molecular weight compounds, as well as natural materials such as, wool, silk, jute, hemp, cotton, linen, sisal, or ramie, are suitable. These nonwoven materials are generally described in Riedel "Nonwoven Bonding Methods and Materials", Nonwoven World, (1987), incorporated herein by reference in its entirety. The preferred film layer substrates of the present invention are polypropylene nonwoven sheets laminated to a film of poly(ethylene-vinyl acetate) or low-density polyethylene (LDPE) having a thickness of about 5 to about 100 μm. An example of a commercially available nonwoven sheet is material number W502FWH, which is commercially available from PGI (Polymer Group International) located in Waynesboro, Va., U.S.A. An example of a commercially available polypropylene/ethylene vinyl acetate (PP/EVA) film is material number DH245, which is commercially available from Clopay Plastics of Cincinnati, Ohio U.S.A.

The opposed surfaces can be created by bonding two substrates together around their periphery thereby forming a pouch, envelope, or pocket with the film side toward the inside of the pouch, envelope or pocket (the side to be filled) and the nonwoven side to the outside. Pockets can also be made in the substrates by thermoforming, mechanical embossing, vacuum embossing, or other acceptable means. Preferred for use herein is thermoforming which is described in "Thermoforming", The Wiley Encyclopedia of Packaging Technology, pp. 668-675 (1986), Marilyn Bakker, ed., incorporated herein by reference in its entirety.

The resulting heat cell can have any geometric shape, e.g., disk, triangle, pyramid, cone, sphere, square, cube, rectangle, rectangular parallelepiped, cylinder, ellipsoid and the like. The preferred shape of the present invention comprises a disk shaped geometry having a cell diameter of from about 0.2 cm to about 5 cm, preferably from about 1 cm to about 4 cm, more preferably from about 2 cm to about 3 cm, and a height of from greater than about 0.2 cm to about 1 cm, preferably from greater than about 0.3 cm to about 0.9 cm, more preferably from about 0.4 cm to about 0.8 cm, and most preferably from about 0.5 cm to about 0.7 cm resulting in a cell volume of from about 0.0045 $cm^3$ to about 20 $cm^3$, preferably from about 0.2 $cm^3$ to about 11 $cm^3$. Alternatively, the shape of the heat cell of the present invention may also be elongated in its geometry, with the long axis parallel to the substrates, having a height of from about 0.2 cm to about 5 cm, preferably from greater than about 0.5 cm to about 1 cm, a width of from about 0.2 cm to about 20 cm, preferably from about 5 cm to about 10 cm, and a length of from about 1 cm to about 20 cm, preferably from about 5 cm to about 10 cm, resulting in a cell volume of from about 0.04 $cm^3$ to about 2000 $cm^3$, preferably from about 1.25 $cm^3$ to about 10 $cm^3$.

The heat cells of the present invention preferably have a cross-section area, per cell, of from about 0.03 $cm^2$ about 20 $cm^2$, more preferably from about 0.1 $cm^2$ to about 15 $cm^2$, even more preferably from about 1 $cm^2$ to about 10 $cm^2$, and most preferably from about 3 $cm^2$ to about 7 $cm^2$. Heat cells with this cross-section area per cell are easily incorporated into body wraps and the like which provide improved conformity with body forms.

The heat cells of the present invention preferably have a premix weight of from about 0.4 grams of premix per cell to about 2.5 grams of premix per cell, more preferably from about 1.0 gram of premix per cell to about 2.4 grams of premix per cell, and most preferably from about 1.5 grams of premix per cell to about 2.3 grams of premix per cell. Heat cells with this weight of premix per cell are also easily incorporated into body wraps and the like which also provide improved conformity with body forms and therefore provides even uniform heat to a target area and improves wearer comfort.

The oxygen permeability of the heat cells of the present invention can be provided by selecting films or film coatings for the film layer substrates forming the pouches, envelopes, pockets, and/or covering layer, that have the specifically desired permeability properties. The desired permeability properties may be provided by microporous films or by films which have pores or holes formed therein. The formation of these holes/pores may be via extrusion cast/vacuum formation or by hot needle aperturing. Oxygen permeability can also be provided in the present invention by perforating at least one of the film layer substrates with aeration holes using, for example, at least one pin, preferably an array of from about 20 to about 60 pins, with, e.g., tapered points and diameters of from about 0.2 mm to about 2 mm, preferably from about 0.4 mm to about 0.9 mm.

Alternatively, after the film layer substrates have been bonded together, enclosing a particulate exothermic composition defined hereinafter in the pocket between them, one side of the heat cell may be perforated with aeration holes using, for example, at least one pin, preferably an array of from about 20 to about 60 pins, with, e.g., tapered points and diameters of from about 0.2 mm to about 2 mm, preferably from about 0.4 mm to about 0.9 mm. The pins are pressed through one side of the heat cell material to a depth of from about 2% to about 100%, preferably from about 20% to about 100%, and more preferably from about 50% to about 100% into the particulate exothermic composition. This hole configuration provides an oxygen diffusion into the heat cell during oxidation of the particulate exothermic composition of from about 0.01 cc $O_2$/min./5 $cm^2$ to about 15.0 cc $O_2$/min./5 $cm^2$ (at 21° C., 1 ATM), preferably from about 0.9 cc $O_2$/min./5 $cm^2$ to about 3 cc $O_2$/min./5 $cm^2$ (at 21° C., 1 ATM). Although there are preferably provided aeration holes in the upper covering film layer, it is also possible to provide aeration holes in the lower covering film layer, and/or both.

The heat cells of the present invention may optionally incorporate a component to be delivered through the skin, wherein the optional component includes active aromatic compounds, non-active aromatic compounds, pharmaceutical actives or other therapeutic agents, and mixtures thereof. The optional component can be incorporated into the heat cells as a separate substrate layer or incorporated into at least one of the film layer substrates. Such active aromatic compounds include, but are not limited to, menthol, camphor, eucalyptus, and mixtures thereof. Such non-active aromatic compounds include, but are not limited to, benzaldehyde, citral, decanal, aldehyde, and mixtures thereof. Such pharmaceutical actives/therapeutic agents include, but are not limited to antibiotics, vitamins, antiviral agents, analgesics, anti-inflammatory agents, antipruritics, antipyretics, anesthetic agents, antifungals, antimicrobials, and mixtures thereof. The heat cells may also comprise a separate substrate layer, or incorporated into at least one of the film layer substrates, a self-adhesive component and/or a sweat-absorbing component.

Exothermic Composition

The heat cells of the present invention comprise a particulate exothermic composition which provides for improved sustained temperature when the heat cells are incorporated into disposable heating devices such as disposable body wraps. The particulate exothermic composition comprises a particulate premix composition and a brine solution.

Components of the particulate premix composition typically include iron powder, carbon, absorbent gelling material, and water, which components are described in detail hereinafter. Likewise, typical components of the brine solution include a metal salt, water, and optionally a hydrogen gas inhibitor such as sodium thiosulfate. The exothermic compositions defined herein are generally prepared by constructing the particulate pre-mix composition and rapidly dosing the pre-mix with the brine solution to result in the formation of heat cells of the present invention. A typical heat cell of the present invention can comprise from about 0.4 grams of pre-mix per cell to about 2.5 grams of premix per cell, and from about 0.4 grams of brine solution per cell to about 1.5 grams of brine solution per cell. Therefore, an exothermic composition of the present invention can comprise a total cell weight, per cell, of from about 0.8 grams to about 4.0 grams, preferably from about 1.5 grams to about 3.5 grams, more preferably from about 2.5 grams, to about 3.0 grams.

The velocity, duration, and temperature of the thermogenic oxidation reaction of the particulate exothermic composition can be controlled as desired by changing the area of contact with air, more specifically, by changing the oxygen diffusion/permeability. Other methods of modifying the exothermic reaction include choice of components within the composition, for example, by choosing a specific component described hereinafter, modifying component particle size, and so forth.

By way of illustration, one particular method of modifying the exothermic reaction involves adding iron powder having a median particle size of about 200 µm, and an absorbent gelling material having a median particle size of about 300 µm, wherein the median particle size ratio of absorbent gelling material to iron powder is 1.5:1. It has been shown that this select ratio of absorbent gelling material to iron powder provides for an exothermic composition that exhibits a fast initial heating temperature and a long duration of heat, which has been a difficult accomplishment of current exothermic compositions. It is believed that current exothermic compositions comprise a high level of moisture that results in water in the interstitial particle voids, which restricts oxygen flow and slows up the rate of the initial heating temperature. It has been found that exothermic compositions which comprise a select median particle size ratio of absorbent gelling material to iron powder provides for excess water being vacant from interstitial particle voids such that faster rates of initial heating temperatures are achieved.

Iron Powder

The particulate exothermic compositions of the present invention comprise one or more iron powder components at concentrations ranging from about 10% to about 90%, preferably from about 30% to about 88%, more preferably from about 50% to about 87%, by weight of the composition.

It is believed that the particulate exothermic compositions defined herein release heat upon oxidation of the iron powder. It is known that iron is the anode for the electrochemical reaction involved in the exothermic oxidation of iron. There is no particular limitation to the purity, kind, size, etc., of the iron powder as long as it can be used to produce heat-generation with electrically conducting water and air. For example, iron powder having a median particle size of from about 50 µm to about 400 µm, preferably from about 100 µm to about 400 µm, more preferably from about 150 µm to about 300 µm, have been found suitable for use herein.

The median particle size of the iron powder, and any other particulate component defined herein, can be determined using a sieve method such as the method disclosed in ASTM Method B214. Generally, the particles are screened through a series of sieves consisting of different sizes, and the weight fraction of particles retained on each screen is measured. The weight fraction of the particles in each screen is then used to construct a cumulative weight distribution curve. The cumulative weight distribution curve is constructed by plotting particle size against the cumulatively added weight percent of particles less than the particle size retained on the next largest sieve. A median diameter is determined from the cumulative weight distribution curve, wherein the median diameter is defined as the particle size that corresponds with 50% of the cumulative weight. Details on constructing a cumulative weight distribution curve is described in "Methods of Presenting Size Analysis Data" in Particle Size Measurement, pages 153-156, 4th Edition, Terrence Allen, (1990), which descriptions are incorporated herein by reference in their entirety. To illustrate the sieve method, about 100 gm+/−0.1 gm of test sample is placed onto the top mesh screen of a stack of U.S. standard sieves wherein each sieve has screen openings that are larger than the screen below it, a lid is placed on the top screen, the stack of sieves are then clamped into a mechanically operated sieve shaker such as a Tyler RoTap shaker, the shaker is allowed to run for 15 minutes while mechanically reproducing the shaking motion that occurs during hand sieving, tapping of the sieve stack occurs during the shaking process to help the particles fall through the mesh screens, after 15 minutes of shaking the material collected on each mesh screen is weighed to the nearest 0.1 grams (gm). The sum of the weights of all the fractions shall not be less than 99.7% of the weight of the test sample. The weights of the fractions retained on each sieve are expressed as percentages of the weight of the test sample to the nearest 0.1%. Any fraction that is less than or equal to 0.04% of the weight of the test sample shall be reported as "TRACE". Any fraction that is greater than or equal to 0.05% of the weight of the test sample shall be reported as 0.1% unless specified to be reported to two decimal places. If a fraction is absent, it shall be reported as 0.0%. The median particle size is then determined.

Preferably, the particulate exothermic compositions comprise a select median particle size ratio of absorbent gelling material defined hereinbelow and the iron powder. Exothermic compositions comprising this select median particle size ratio of components have been shown to provide for heat cells that have improved heat application and that have the ability to resist compositional changes such as resistance to particle segregation. The median particle size ratio of absorbent gelling material to iron powder typically ranges from about 10:1 to about 1:10, preferably from about 7:1 to about 1:7, more preferably from about 5:1 to about 1:5, and most preferably from about 3:1 to about 1:3.

The heat cells of the present invention are typically small as compared to current heat cells, and excess levels of exothermic composition cannot be used to compensate for particle segregation effects. In fact, adding excess levels of exothermic composition can result in significant changes in the thermal performance of heat cells. It has been found that particle segregation effects are reduced by using iron powder having a median particle size within the ranges defined herein, especially by using iron powder in a ratio combination of absorbent gelling material to the iron powder. It is believed that the reaction rate of exothermic compositions is controlled by the porosity of the exothermic compositions, in other words the rate at which heat cells emit heat is impacted by the packing behavior of the particles (i.e., interstitial particle void volume) and by the amount of water present in the exothermic composition. The iron powder defined herein provides for low packing behavior, whereas the absorbent gelling material prevents water from entering particle voids, thus resulting in heat cells that exhibit fast initial heating temperatures and long duration of heat for treating temporary or chronic body aches and pain.

Nonlimiting examples of suitable sources for the iron powder of the present invention include cast iron powder, reduced iron powder, electrolytic iron powder, scrap iron powder, sponge iron, pig iron, wrought iron, various steels, iron alloys, treated varieties of these iron sources, and mixtures thereof. Sponge iron is preferred.

Sponge iron is one source of the iron powder, which may be particularly advantageous due to the high internal surface area of sponge iron. As the internal surface area is orders of magnitude greater than the external surface area, reactivity may not be controlled by particle size. Nonlimiting examples of commercially available sponge iron include M-100 and F-417, which are available from the Hoeganaes Corporation located in New Jersey, U.S.A.

Sponge iron is a material utilized in the steel making industry as a basic source for the production of steel. Without intending to be limited by any method of production, sponge iron may be produced by exposing hematite ($Fe_2O_3$) iron ore in comminuted form to a reducing gas environment at temperatures somewhat below blast furnace temperatures. Sponge iron is more specifically disclosed, including the production of sponge iron, in U.S. Pat. Nos. 2,243,110; 2,793,946; 2,807,535; 2,900,247; 2,915,379; 3,128,174; 3,136,623; 3,136,624; 3,136,625; 3,375,098; 3,423,201; 3,684,486; 3,765,872; 3,770,421; 3,779,741; 3,816,102; 3,827,879; 3,890,142; and 3,904,397; which disclosures are incorporated by reference herein.

While oxygen is necessary for the oxidation reaction of iron to occur, an internal oxygen source is not required in the heat cells of the present invention, however, oxygen-producing chemical materials may be incorporated in the particulate exothermic composition at the time of preparation thereof without changing the scope of the present invention. The oxygen sources used for the purpose of this invention include air and artificially made oxygen of various purity. Among these oxygen sources, air is preferred since it is the most convenient and inexpensive.

Carbon

The particulate exothermic compositions of the present invention comprise one or more carbon components at concentrations ranging from about 1% to about 25%, preferably from about 1% to about 15%, more preferably from about 1% to about 10%, by weight of the composition.

Nonlimiting examples of carbon suitable for use herein include activated carbon, non-activated carbon, and mixtures thereof. The carbon component has a median particle size of from about 25 μm to about 200 μm, preferably from about 50 μm to about 100 μm. Activated carbon is preferred.

Activated carbon serves as the cathode for the electrochemical reaction involved in the exothermic oxidation of iron. However, the cathode capabilities can be extended by additionally using non-activated carbon powder, i.e., carbon blended to reduce cost. Therefore, mixtures of the above carbons are useful in the present invention as well.

Activated carbon is extremely porous in the inner structure giving it particularly good oxygen adsorption capabilities. In fact, activated carbon has the ability to adsorb oxygen extremely well when the activated carbon is wetted, thus allowing for the activated carbon to function as a catalyst in the electrochemical reaction.

Moreover, activated carbon can absorb water well, and can serve as a water-holding material. Further, active carbon can adsorb odors such as those caused by the oxidation of iron powder.

Activated carbon prepared from coconut shell, wood, charcoal, coal, bone coal, and the like, are suitable for use herein, but those prepared from other raw materials such as animal products, natural gas, fats, oils and resins are also useful in the particulate exothermic compositions of the present invention. There is no limitation to the kinds of activated carbon used, however, the preferred activated carbon has good oxygen adsorption capabilities. An example of a commercially available activated carbon includes the activated carbon available from MeadWestvaco located in Covington, Va. (USA).

To provide for fast heat up of the exothermic composition while sustaining thermal duration, the exothermic compositions should have more absorbent gelling material than the activated carbon. It has been shown that if the absorbent gelling material is less than the activated carbon, then the exothermic reaction becomes sensitive to the moisture content and will not heat up as fast. Without being bound by theory, it is believed that this is due to the competition for moisture between the absorbent gelling material and activated carbon, and for the exothermic reaction to proceed the activated carbon needs to be sufficiently wetted in order for it to function as a catalyst for adsorbing oxygen.

Additionally, the amount of carbon in the particulate exothermic compositions defined herein should be minimal in order to maximize the interstitial particle void volume. Carbon is typically the finest particle component and excess carbon would result in the carbon filling up the interstitial particle void volume. It has been found that the amount of carbon needed for the exothermic reaction is significantly lower than what is used in current exothermic compositions because of the relatively high level of absorbent gelling material used. Therefore, the carbon is mainly used for its catalytic activity and minimally for its water retention property.

A low level of carbon is also highly desirable for the method of making heat cells of the present invention since a low level of carbon provides for the pre-mix to rapidly absorb the brine solution. This significantly increases the rate of the method of making the heat cells defined herein.

Absorbent Gelling Material

The particulate exothermic compositions of the present invention comprise one or more absorbent gelling materials at concentrations ranging from about 1% to about 25%, preferably from about 1% to about 15%, more preferably from about 1% to about 10%, by weight of the composition.

The absorbent gelling material suitable for use herein enables the retention of water physically or chemically within the particulate exothermic compositions of the present invention. In particular, the absorbent gelling material serves the function of gradually supplying water to the iron powder component, wherein the water is released at a controlled rate. While not intending to be bound by theory, it is believed that the absorbent gelling material can prevent or inhibit water from entering, or being maintained in, the interstitial voids of the various particles of the exothermic compositions, thereby helping to prevent or inhibit flooding.

Nonlimiting examples of suitable absorbent gelling materials include those absorbent gelling materials that have fluid-absorbing properties and can form hydrogels upon contact with water. One specific example of such an absorbent gelling material is the hydrogel-forming, absorbent gelling material that is based on a polyacid, for example polyacrylic acid. Hydrogel-forming polymeric materials of this type are those which, upon contact with liquids such as water, imbibe such fluids and thereby form the hydrogel. These preferred absorbent gelling materials will generally comprise substantially water-insoluble, slightly cross-linked partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, specific suitable absorbent gelling materials include hydrolyzed acrylonitrile grafted starch, acrylic acid grafted starch, polyacrylate, maleic anhydride-based copolymer, and combinations thereof. The polyacrylates and acrylic acid grafted starch materials are preferred. Nonlimiting examples of commercially available polyacrylates include those polyacrylates which are available from Nippon Shokubai located in Chattanooga, Tenn. (U.S.A.).

The absorbent gelling material has a median particle size of from about 300 μm to about 800 μm, preferably from about 400 μm to about 800 μm, more preferably from about 500 μm to about 800 μm. Absorbent gelling materials having a median particle size of 300 μm or greater have been shown to contribute to minimal or no segregation effects. Reducing segregation effects provides for improved sustained temperature such that the desired therapeutic heat benefits are achieved without any adverse events such as skin burns. Reducing segregation effects also allows for the high speed production of disposable heating devices comprising a plurality of heat cells that provide for up to twenty-four hours of therapeutic heat.

As described hereinabove, the particulate exothermic compositions defined herein preferably have select median particle size ratios of absorbent gelling material to iron powder. It has been shown that exothermic compositions comprising the defined select median particle size ratios of these components, exhibit minimal or no segregation effects which result in exothermic compositions that meet the intended thermal behavior for the desired therapeutic heat benefits.

In addition to the absorbent gelling material, the particulate exothermic compositions of the present invention can optionally comprise other water-holding materials that have capillary function and/or hydrophilic properties. These optional water-holding materials can be included in the particulate exothermic compositions at concentrations ranging from about 0.1% to about 25%, preferably from about 0.5% to about 20%, more preferably from about 1% to about 15%, by weight of the composition. Nonlimiting examples of such optional water-holding materials include vermiculite, porous silicates, wood powder, wood flour, cotton, paper, vegetable matter, carboxymethylcellulose salts, inorganic salts, and mixtures thereof. The absorbent gelling material and optional water-holding materials are further described in U.S. Pat. Nos. 5,918,590 and 5,984,995; which descriptions are incorporated by reference herein.

Metal Salt

The particulate exothermic composition of the present invention comprises one or more metal salts at concentrations ranging from about 0.5% to about 10%, preferably from about 0.5% to about 7%, more preferably from about 1% to about 5%, by weight of the composition.

The metal salts suitable for use herein include those metal salts that serve as a reaction promoter for activating the surface of the iron powder to ease the oxidation reaction with air and provide electrical conduction to the exothermic composition to sustain the corrosive reaction. In general, several suitable alkali, alkaline earth, and transition metal salts exist which can be used, alone or in combination, to sustain the corrosive reaction of iron.

Nonlimiting examples of suitable metal salts include sulfates, chlorides, carbonate salts, acetate salts, nitrates, nitrites, and mixtures thereof. Specific nonlimiting examples of sulfates include ferric sulfate, potassium sulfate, sodium sulfate, manganese sulfate, magnesium sulfate, and mixtures thereof. Specific nonlimiting examples of chlorides include cupric chloride, potassium chloride, sodium chloride, calcium chloride, manganese chloride, magnesium chloride cuprous chloride, and mixtures thereof. Cupric chloride, sodium chloride, and mixtures thereof are the preferred metal salts. An example of a commercially available sodium chloride includes the sodium chloride available from Morton Salt located in Chicago, Ill. (USA).

Water

The particulate exothermic compositions of the present invention comprise water at concentrations ranging from about 1% to about 35%, preferably from about 5% to about 33%, by weight of the composition. The water suitable for use herein can be from any appropriate source. For example, tap water, distilled water, or deionized water, or any mixture thereof, is suitable for use herein.

It is known that the thermal performance of heat cells is highly sensitive to moisture level, and a typical heat cell can comprise water concentrations at or above about 27% to sustain the heating temperature of the heat cell. However, the inclusion of high concentrations of water at levels of about 27% or above can result in slower than desired initial heating temperatures. Therefore, the ability to rapidly reach the desired temperature for a therapeutic benefit and the ability to sustain the temperature are difficult to achieve. It has been found, however, that the particulate exothermic compositions of the present invention not only provide for heat cells that are highly effective in maintaining a sustained, controlled, and consistent temperature, but also provide for heat cells that have fast initial heating temperatures, thus resulting in heat cells that provide the desired therapeutic heat benefits without any adverse events such as skin burns. This is achieved by incorporating a sufficient weight ratio of water to absorbent gelling material such that the particulate exothermic compositions have a high internal water retention and high interstitial particle void volumes. The particulate exothermic compositions of the present invention comprise a weight ratio of water to absorbent gelling material of from about 3:1 to about 9:1, preferably from about 4:1 to about 7:1, by weight of the exothermic composition.

Moreover, current heat cells typically comprise a high level of water to increase the length of time to sustain the heating temperature of the heat cells. Thus, the exothermic compositions of the present invention can comprise a high level of water and be constructed at lower cell weight levels than current heat cells. Therefore, the exothermic compositions of the present invention are utilized more effectively with high water concentration, and lesser exothermic composition is needed to achieve the desired heating temperature duration time.

Optional Components

The exothermic compositions of the present invention may further comprise one or more other optional components known or otherwise effective for use in exothermic compositions, provided that the optional components are physically and chemically compatible with the compositional components described hereinabove, or do not otherwise unduly impair product stability, aesthetics, or performance. Other optional components suitable for use herein include materials such as agglomeration aids including corn syrup, maltitol syrup, crystallizing sorbitol syrup, and amorphous sorbitol syrup; dry binders including microcrystalline cellulose, microfine cellulose, maltodextrin, sprayed lactose, co-crystallized sucrose and dextrin, modified dextrose, mannitol, pre-gelatinized starch, dicalcium phosphate, and calcium carbonate; oxidation reaction enhancers including elemental chromium, manganese, copper, and compounds comprising said elements; hydrogen gas inhibitors including inorganic and organic alkali compounds, and alkali weak acid salts, specific nonlimiting examples include sodium thiosulfate, sodium sulfite, sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, inorganic compounds including silica powder, porous silica gel, sodium sulfate, barium sulfate, iron oxides, and alumina; anti-caking agents such as tricalcium phosphate and sodium silicoaluminate; and mixtures thereof. Such components also include thickeners such as cornstarch, potato starch, carboxymethylcellulose, and alpha-starch, and surfactants such as those included within the anionic, cationic, nonionic, zwitterionic, and amphoteric types. Still other optional components may be included within the compositions or articles herein, as appropriate, including extending agents such as metasilicates, zirconium, and ceramics, and mixtures thereof. The other optional components can be included in the particulate exothermic compositions at concentrations ranging from about 0.01% to about 35%, preferably from about 0.1% to about 30%, by weight of the composition.

Method of Manufacture

The particulate exothermic compositions of the present invention may be prepared by any known or otherwise effective technique suitable for providing an exothermic composition that provides a therapeutic heat benefit. The particulate exothermic compositions of the present invention are preferably prepared using conventional blending techniques. Suitable methods of blending the components of the particulate exothermic compositions of the present invention are more fully described in U.S. Pat. No. 4,649,895 to Yasuki et al., issued Mar. 17, 1987, which descriptions are incorporated by reference herein.

A typical technique of blending the components of the particulate exothermic compositions involve adding carbon to a blender or mixer, followed by adding a small amount of the total water, and then mixing the carbon/water combination. Usually enough water is added to assist in blending while avoiding escalated corrosion. Mixing is stopped and an absorbent gelling material is added to the carbon/water combination. Mixing is resumed until all the components are mixed thoroughly, and then iron powder is added and mixed. The composition is then blended until thoroughly mixed to form a particulate pre-mix. Sodium chloride, optionally an hydrogen gas inhibitor such as sodium thiosulfate, and the remaining water are separately mixed to form a brine solution which is then added to the iron powder pre-mix to form a particulate exothermic composition that is used in the construction of a heat cell of the present invention.

Individual heat cells can typically be prepared by adding a fixed amount of the particulate pre-mix composition to a pocket in a film layer substrate sheet such as the pocket in a polypropylene nonwoven/LDPE film layer substrate sheet. In this process, water or brine is rapidly dosed on top of the pre-mix composition, and a flat sheet of a polypropylene nonwoven/poly(ethylene-vinyl acetate) film layer substrate is placed over the cell with the poly(ethylene-vinyl acetate) film side facing the LDPE film side of the preformed pocket containing sheet. The film layers of the two sheets are bonded together using a low heat, forming a unified structure. The resulting heat cell contains the particulate exothermic composition sealed in the pocket between the two film layer substrate sheets.

Alternatively, individual heat cells can be prepared by using vacuum to form a pocket. That is, vacuum is used to draw the film layer substrate surface into a mold as the particulate pre-mix composition is placed on top of the film layer substrate surface directly over the mold. The particulate pre-mix composition drops into the vacuum formed pocket and is held in place by the vacuum exerted upon the particulate pre-mix composition in the bottom of the mold. Next, a brine solution is rapidly dosed on top of the pre-mix composition. A second film layer substrate surface is then placed over the first film layer substrate surface, such that the particulate exothermic composition is between the two surfaces. The particulate exothermic composition is then sealed between the first and second film layer substrate surfaces.

The resultant heat cells can be used alone, or as a plurality of heat cells, wherein the heat cells can be incorporated into various disposable heating devices such as disposable body wraps. Typically, the body wraps have a means for retaining the wraps in place around various parts of the body, such as knee, neck, back, etc. and can comprise any number of styles and shapes, wherein the retaining means include a fastening system such as a reclosable two-part hook and loop fastening system.

The resultant heat cells are preferably packaged in a secondary air-impermeable package to prevent the oxidation reaction from occurring until desired as described in the aforementioned U.S. Pat. No. 4,649,895, already incorporated herein by reference. Alternatively, air impermeable removable adhesive strips can be placed over the aeration holes in the heat cells such that, when the strips are removed, air is allowed to enter the heat cell, thus activating the oxidation reaction of the iron powder.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

The particulate exothermic compositions exemplified below are prepared by using conventional blending techniques to form the particulate exothermic compositions, wherein the resultant compositions provide for the construction of heat cells of the present invention.

A premix is prepared by adding activated carbon and water into a blender or mixer such as a Littleford Day Mixer, and mixing for about ten minutes. An absorbent gelling material such as a polyacrylate is then added, and the mixture is mixed for about 10 minutes. Next, iron powder such as sponge iron is added to the mixer, and the resultant premix is mixed for about 5 minutes.

Approximately 2.2 grams of the resultant premix composition are added to a preformed pocket, which has been thermoformed to form the pocket, in a sheet of polypropylene nonwoven that has been coated with a film of LDPE.

Next, a brine solution is prepared by adding water, a metal salt such as sodium chloride, and optionally sodium thiosulfate into a mixer and mixing for about fifteen minutes. The resultant brine solution is then rapidly dosed onto the premix composition to result in the construction of one or more heat cells of the present invention.

A flat polypropylene nonwoven sheet coated with poly(ethylene-vinyl acetate) is then placed over the heat cell and heat bonded to the bottom sheet. Material around the heat cell is trimmed to provide 2.5 cm of excess material around the perimeter of the cell. One hundred pins of approximately 0.5 mm diameter are pressed simultaneously into one side of the cell until they penetrate approximately 100% into the exothermic composition, but not through the bottom sheet. This perforation process results in a diffusive $O_2$ permeability of about 1 cc/min./5 cm$^2$ (at 21° C., 1 ATM). The cell begins to generate heat shortly after the brine is added to the particulate composition, therefore the top and bottom sheets are bonded and the finished heat cell is quickly packaged in an air tight secondary packaging for future use.

The resultant heat cells can be incorporated into disposable heating devices including disposable body wraps such as back wraps, knee wraps, joint wraps, menstrual wraps, neck-to-arm wraps, and so forth.

| Particulate Exothermic Compositions | | | |
| --- | --- | --- | --- |
| Component | Example 1 (Wt. %) | Example 2 (Wt. %) | Example 3 (Wt. %) |
| Iron powder | 60.40 | 56.75 | 58.70 |
| Activated Carbon | 4.05 | 3.81 | 3.94 |
| Absorbent Gelling Material | 5.09 | 4.78 | 4.94 |
| Sodium Chloride | 3.02 | 3.47 | 1.38 |
| Sodium Thiosulfate | 0.38 | 0.43 | — |
| Water | 27.06 | 30.76 | 31.04 |

While particular embodiments suitable for use in the particulate exothermic compositions of the present invention have been described, it will be obvious to those skilled in the art that various changes and modifications of the present invention can be made without departing from the spirit and scope of the invention. It is intended to cover, in the appended claims, all such modifications that are within the scope of this invention.

What is claimed is:

1. A heat cell comprising a particulate exothermic composition wherein the particulate exothermic composition comprises: (a) from about 10% to about 90% by weight of iron powder having a median particle size of from about 50 μm to about 400 μm; (b) from about 1% to about 25% by weight of a carbon selected from the group consisting of activated carbon, non-activated carbon, and mixtures thereof; (c) from about 1% to about 25% by weight of an absorbent gelling material having a median particle size of from about 300 μm to about 800 μm; and (d) from about 1% to about 35% by weight of water; wherein the particulate exothermic composition comprises a median particle size ratio range of absorbent gelling material to iron powder of less than 3:1 to 1:3; wherein the particles of the particulate exothermic composition are combined in a pocket, formed in a unified structure comprising at least two opposed surfaces, wherein at least one surface is oxygen permeable; and wherein the particulate exothermic composition in the pocket has interstitial particle void volume.

2. The heat cell of claim 1 wherein the particulate exothermic composition comprises a median particle size ratio of absorbent gelling material to iron powder of about 1:1.

3. The heat cell of claim 1 wherein the particulate exothermic composition comprises from about 50% to about 87% by weight of the iron powder.

4. The heat cell of claim 3 wherein the iron powder has a median particle size of from about 150 μm to about 300 μm.

5. The heat cell of claim 4 wherein the iron powder is selected from the group consisting of cast iron powder, reduced iron powder, electrolytic iron powder, scrap iron powder, pig iron, sponge iron, wrought iron, steel, iron alloy, and mixtures thereof.

6. The heat cell of claim 5 wherein the iron powder is sponge iron.

7. The heat cell of claim 1 wherein the particulate exothermic composition comprises from about 1% to about 10% by weight of the activated carbon, non-activated carbon, and mixtures thereof.

8. The heat cell of claim 7 wherein the activated carbon is prepared from materials selected from the group consisting of coconut shell, wood, charcoal, coal, bone coal, animal products, natural gas, fats, oils, resins, and mixtures thereof.

9. The heat cell of claim 1 wherein the particulate exothermic composition comprises from about 1% to about 15% by weight of the absorbent gelling material.

10. The heat cell of claim 9 wherein the absorbent gelling material is a hydrogel-forming polymeric material.

11. The heat cell of claim 10 wherein the hydrogel-forming polymeric material is selected from the group consisting of hydrolyzed acrylonitrile grafted starch, acrylic acid grafted starch, polyacrylate, maleic anhydride-based copolymer, and mixtures thereof.

12. The heat cell of claim 1 wherein the particulate exothermic composition further comprises from about 0.5% to about 10% by weight of a metal salt.

13. The heat cell of claim 12 wherein the metal salt is selected from the group consisting of alkali metal salts, alkaline earth metal salts, transition metal salts, and mixtures thereof.

14. The heat cell of claim 13 wherein the metal salt is selected from the group consisting of sodium chloride, cupric chloride, and mixtures thereof.

15. The heat cell of claim 1 wherein the heat cell has a cross-section area of from about 2 cm$^2$ to about 10 cm$^2$.

16. The heat cell of claim 15 wherein the heat cell is in a shape selected from the group consisting of disk, triangle, pyramid, cone, sphere, square, cube, rectangle, rectangular parallelepiped, cylinder, ellipsoid, and combinations thereof.

17. The heat cell of claim 1 wherein the heat cell has a total cell weight of from about 0.8 grams to about 4.0 grams.

18. The heat cell of claim 17 wherein the heat cell is incorporated into disposable heating articles selected from the group consisting of back wraps, knee wraps, neck wraps, menstrual wraps, joint wraps, and neck-to-arm wraps.

19. The heat cell of claim 15 wherein the heat cell is elongated in shape and has a cell volume of about 1.25 to about 10 cm$^3$.

* * * * *